(12) United States Patent
Brenner et al.

(10) Patent No.: US 12,245,894 B2
(45) Date of Patent: Mar. 11, 2025

(54) SYSTEM AND METHOD FOR NON-INVASIVE REAL TIME ASSESSMENT OF CARDIOVASCULAR BLOOD PRESSURE

(71) Applicants: Alexander Brenner, Haifa (IL); Felix Brenner, Haifa (IL); Avraham Lorber, Haifa (IL)

(72) Inventors: Alexander Brenner, Haifa (IL); Felix Brenner, Haifa (IL); Avraham Lorber, Haifa (IL)

(73) Assignee: Pi-Harvest Holding AG, Schaffhausen (CH)

( * ) Notice: Subject to any disclaimer, the term of this patent is extended or adjusted under 35 U.S.C. 154(b) by 0 days.

(21) Appl. No.: 16/797,357

(22) Filed: Feb. 21, 2020

(65) Prior Publication Data
US 2021/0259666 A1 Aug. 26, 2021

(51) Int. Cl.
| | | |
|---|---|---|
| A61B 8/08 | (2006.01) | |
| A61B 5/021 | (2006.01) | |
| A61B 6/50 | (2024.01) | |
| A61B 8/00 | (2006.01) | |
| A61B 8/04 | (2006.01) | |
| G06T 7/00 | (2017.01) | |

(52) U.S. Cl.
CPC .............. *A61B 8/5223* (2013.01); *A61B 8/04* (2013.01); *A61B 8/54* (2013.01); *A61B 8/56* (2013.01); *G06T 7/0012* (2013.01); *A61B 5/021* (2013.01); *A61B 6/507* (2013.01); *G06T 2207/30048* (2013.01)

(58) Field of Classification Search
CPC ........... A61B 8/5223; A61B 8/54; A61B 8/58; A61B 8/04
See application file for complete search history.

(56) References Cited

U.S. PATENT DOCUMENTS

| | | | | |
|---|---|---|---|---|
| 2004/0129082 A1* | 7/2004 | Frinking | .............. | G01N 29/036 73/590 |
| 2009/0171201 A1* | 7/2009 | Olson | .................. | A61B 8/0883 600/438 |
| 2018/0316781 A1* | 11/2018 | Salem | ................... | H04L 67/306 |

FOREIGN PATENT DOCUMENTS

| | | | | |
|---|---|---|---|---|
| WO | WO-2010147055 A1 * | 12/2010 | ............. | A61B 8/481 |
| WO | WO-2018024868 A1 * | 2/2018 | ......... | A61B 5/02156 |

OTHER PUBLICATIONS

Brenner et al. ("A System and Method for Non-Invasive Measurement of Cardiovascular Blood Pressure," (Jul. 24, 2018) Biomedical Journal of Scientific & Technical Research, vol. 7, Issue 2) (Year: 2018).*

(Continued)

*Primary Examiner* — Joel Lamprecht
*Assistant Examiner* — Ashish S Jasani

(57) ABSTRACT

A system and method of measurement and calculation of intracardiac pressures based on non-invasive medical imaging is presented, wherein the pressure measurements are performed by means of the image stream with further estimation of the volumes of oscillating traceable regions within the heart vicinity. The volume estimates are tied to pressure values in such oscillating traceable regions as left/right atria and ventricles, pulmonary artery and aorta. The invention permits to assess non-invasively and in real time the pressure in any part of the heart and large blood vessels, and calculate the major markers of heart failure, cardiomyopathy, ventricular ischemia, infarction and other heart related diseases.

2 Claims, 12 Drawing Sheets

(56) References Cited

OTHER PUBLICATIONS

Noninvasive Intracardiac Pressure Measurements Using Subharmonic Aided Pressure Estimation: Proof of Concept in Humans, (Nov. 2017) Ultrasound Med Biol. Nov. 2017 ; 43(11): 2718-2724) (Year: 2017).*

* cited by examiner

SYSTEM AND METHOD FOR NON-INVASIVE REAL TIME ASSESSMENT OF CARDIOVASCULAR BLOOD PRESSURE

PRESENT FIELD

The present invention belongs to the field of medical imaging for the non-invasive real time determination of a cardiovascular blood pressure in the heart vicinity.

BACKGROUND

Diseases including congestive heart failure (CHF), abdominal aortic aneurysm (AAA), pulmonary artery hypertension (PAH), are a major cause of premature death. There is a desire to be able to provide an advantageous monitoring of intravascular and/or intracardiac blood pressure, with continuous monitoring. Based on such blood pressure measurements, diagnosis and treatment of users can be based on a unique level, preventing substantial populations from premature death.

Currently, the monitoring of intracardiac blood pressures is possible only during diagnostic catheterization procedure, an invasive process when a pressure meter is physically penetrated into the chamber/artery in question, and is performed under certain medical conditions from time to time.

Implantable sensors used for post-operative continuous monitoring may be introduced during such catheterization procedure and left in the desired heart region. Such invasive measurements of intra-cardiac pressures are desired to be minimized due to complexity of the procedure and related complications and risk.

There are two types of implantable sensors. Active implantable sensors that need a rechargeable energy source, which is related to a number of apparent disadvantages. Passive implantable sensors which are typically electromagnetic, providing an electromagnetic signal when irradiated from the external to the human body source of electromagnetic energy mainly in radio frequencies (RF). These sensors have a considerable drawback due to the locality of their position and ability to measure the pressure only in their circumference, also these sensors have electronics incorporated and have thus related disadvantages, such as issues of biocompatibility, size or reliability of the implanted sensor over time. Moreover, while a part of the RF energy reaches the implanted RF sensor, a considerable amount of the RF energy is absorbed by the body which may cause potential problems in living organisms. Energy transmitted from outside the body may be converted in these implants to power the electronics, make measurements and transmit measurement results back to the outer detecting system. Such detecting system, positioned externally to the human body registers the electromagnetic field radiated by the circuit of the implanted sensor and converts it to readable data.

An example of electromagnetic sensor is described in the U.S. Pat. No. 7,245,117 B1 with the title "Communicating with implanted wireless sensor", the resonant frequency of a sensor is determined for energizing the system to burst the RF energy at predetermined frequencies and amplitudes. A similar technology is described in the U.S. Pat. No. 8,894,582 B2.

Cardiovascular ultrasound measurements are known, but restricted to either catheter based ultrasound transceivers introduced into the body, or regular and Doppler ultrasound measurements. Blood pressure in peripheral vessels may be measured non-invasively from the outside of the body using ultrasound. However, calibration to actual pressure values of such ultrasound-based methods is complex and not always reliable. Moreover, such methods cannot selectively measure pressure at specific depths and places in the body, e.g. in the aorta or the heart. Other, non-invasive techniques include methods to examine dimensions of blood vessels, or methods based on examining blood flow and are based on Doppler ultrasound or other ultrasound imaging methods, as disclosed, for instance, in U.S. Pat. Nos. 5,411,028, 5,477,858 A, 5,544,656, 6,814,702 B2, 5,724,973 A, US 20140081144 A1, EP 1421905 A1, U.S. Pat. No. 7,128,713 B2, WO 2007087522 A2, US 20080119741 A1, U.S. Pat. No. 7,736,314 B2, US 20130197367 A1, or US 20130006112.

For example in U.S. Pat. No. 5,520,185 A with the title "Method for recognition and reduction of blood speckle in blood vessel imaging system", a method for enhancing an intravascular ultrasound blood vessel image system is disclosed. It is explained how ultrasound echoes representing vessel walls are distinguished from ultrasound echoes from blood flow by using a classifier which employs the mean and variance of the raw data of greyscale intensities as acquired directly from an ultrasound scanner-detector.

In U.S. Pat. No. 5,800,356 with the title "Ultrasonic diagnostic imaging system with Doppler assisted tracking of tissue motion", a method for tracing the border of tissue through temporarily acquired scan lines using velocity information corresponding to the tissue edges to trace the denoted border is disclosed.

In U.S. Pat. No. 6,258,031 B1 with the title "Ultrasound diagnostic apparatus", the velocity of a blood flow and velocity of a blood vessel walls at the same time are measured by an ultrasound with phase detecting.

In US 20090171205 A1 with the title "Method and system for locating blood vessels", a method utilizing the direct ultrasound sounding for detecting the blood vessels and precisely determining of their depth and diameter is disclosed.

In U.S. Pat. No. 8,469,887 B2 with the title "Method and apparatus for flow parameter imaging", a method using pulse-wave spectral Doppler imaging allowed to obtain an ultrasound image as a sectional image of the blood vessel, including the inner and outer walls.

Other methods and systems for blood pressure measurements in the blood vessels using Doppler ultrasound imaging are disclosed in: U.S. Pat. No. 5,749,364 A1, WO 20010000 A9, US 20070016037 A1, US 20050015009 A1, US 20140180114 A1, US 20140148702, U.S. Pat. No. 8,968,203 B2, US 20150289836.

In US 20150230774 A1 with the title "Blood pressure monitor and method", non-invasive continuous real-time monitoring of an arterial blood pressure is disclosed using Doppler probes for systolic and diastolic blood pressure.

In the U.S. Pat. No. 7,404,800B2 a hybrid Left Ventricular End-Diastolic Pressure (LVEDP) monitor is disclosed. The patent refers to unspecified non-invasive pressure measurement devices ("barographs"), yet does not disclose how they produce the "pressure waveform" that is therein used for subsequent analysis and unlike current disclosure does not rely on multi-dimensional image processing.

The above discussed non-invasive ultrasound or Doppler ultrasound methods for the examination of the blood vessels have a number of explicit deficiencies and it is desirous to overcome each of these deficiencies, alone or in combination. Deficiencies include but are not limited to the below:

1. Reproducibility and accuracy of the examination of the blood vessel is highly dependent on the correct orientation of the ultrasound beam's propagation direction (the axis of the ultrasound transducer) relatively to the vessel's longitudinal axis being interrogated. The speed of blood flow is measured by converting of the value of the shift of the Doppler frequency $\Delta f$ using the Doppler equation:

$$V=(c\times\Delta f)/(2f_0\times\cos\alpha),$$

where V is the velocity of the blood flow, c is the speed of sound in the tissue, $f_0$ is the initial frequency of the signal, and a is the angle between the direction of the blood flow and the axis of the ultrasound beam. The angle $\alpha$ strongly affects the value of the measured Doppler frequency $\Delta f$ which in turn is used to calculate of the speed of the organic reflectors in the blood flow.

2. Reliability and precision of blood vessel examination including blood pressure measurement based on ultrasound can be improved. For instance, the Doppler frequency spectra display the blood flow information from a certain area at a given depth, (control volume), and do not provide information about blood flow in other parts of the vessel which are visible on the ultrasound image. Therefore, in case choosing an inadequate control volume (ex., when cos $\alpha$~0) all diagnostic information will be incorrect.

3. References to non-specified devices and amplitude sensors (such as in U.S. Pat. No. 7,404,800B2) that produce the intracardiac pressure without further explanations.

Insufficient accuracy of results from hemodynamic measurements in blood vessels using certain Doppler methods are well documented. For example, in: S. B. Coffi, D. Th. Ubbink and D. A. Legemate. Non-invasive Techniques to Detect Subcritical Iliac Artery Stenosis. Eur. J. Vascular and Endovascular Surgery, 29, 2005; Ricardo Cesar, Rocha Moreira. Comparative study of Doppler ultrasonography with arteriography in the evaluation of aortic occlusive disease. Journal Vascular Brasileiro, 8, January/March 2009; or Vilhelm Schaberle. Ultrasonography in Vascular Diagnosis. A Therapy-Oriented Textbook and Atlas. Second Edition. Springer Heidelberg-Dordrecht-London-New-York, 2011.

The article Gernot Schulte-Altedorneburg, Dirk W. Droste, Szabolcs Felszegny, Monica Kellerman et al., Accuracy in vivo Carotid B-mode Ultrasound Compared with Pathological Analysis: Intima-Media Thickening, Lumen Diameter and Cross-Sectional Area. Stroke: Journal of the American Heart Association, 2001 demonstrates an insufficient accuracy of the results obtained for the examination of blood vessels using of the ultrasound B-mode imaging only.

Several patents are dedicated to using passive sensors placed in the human body and interacting with an external ultrasound source for analysis of physiological parameters of the human organism, as for instance U.S. Pat. Nos. 5,619,997 A, 5,989,190 A, 6,083,165 A, or US 20030176789 A1. However, these devices and methods have a number of drawbacks, namely the following:

1. The disclosures in U.S. Pat. Nos. 5,619,997 A, 5,989, 190 A, 6,083,165 A consist in the suggestion that the physical parameters (pressure, temperature, viscosity) defining the state of the medium (including the human body) are determined as a functional relationship P=f(v), where P is the physical parameter and v is the frequency of the ultrasound wave reflected by a passive sensor placed in the medium which is different from the frequency of the primary ultrasound beam due the energy absorption by the sensor.

2. The disclosure in patent application US 20030176789 A1 suggests that the value of a specific physical parameter, such as the pressure, associated with the specific state of any medium (including the human body) is determined as the result of the frequency analysis of the acoustic signal reflected by the passive sensor implanted into the medium. The passive sensor has to be equipped with two parallel to each other reflective surfaces and the reflected signal is the result of the interference of the two acoustic signals: the first signal is reflected by the first reflective surface and second signal reflected by the second reflective surface.

The frequency analysis of the resultant signal permits allocate the frequencies of the maximal attenuation of the intensity and the value of the specific physical parameter is determined on the basis of the correlation relationships between the values of the parameters and the frequencies of the maximum attenuation of the resultant signal. The knowledge of the correlation between the values of the parameters and the frequencies is not sufficient to determine the functional relationship P=F(v). The method is dependent of the frequencies of both the direct and reflected signals, It is desired to provide a more simple method and system that is independent of the frequencies of both the direct and reflected signals which are also present in the following patent: US 20070208293 A1 "Methods and devices for non-invasive pressure measurement in ventricular shunts". This disclosure relates to a ventricular shunt including a pressure-sensitive body that changes its dimensions in response to the pressure of the cerebrospinal fluid within the shunt.

The difference of US 20070208293 A1 from current document lies in several aspects. First, the flow of cerebrospinal fluid is quasi-stationary unlike the turbulent blood flow such as inside the heart chambers which are the subject of the current disclosure. Second, the system from US 20070208293 A1 is tracking the distance changes between the transducer and ultrasonic beam reflecting gas-filled capsule, while in the current description the pressure is determined/estimated as the function of volumes of oscillating traceable regions in a series of images produced by medical imaging device placed fully outside of the body, regardless of presence or absence of any implanted devices. By an oscillating traceable region we mean a region appearing on most images of the series corresponding to the physiological domain where the pressure is measured or calculated, typically one or more of heart chambers, pulmonary artery and/or aorta.

On the other hand, we note the successful approach of the linear regression modeling of the maximal value of the Left Atrium pressure changes through the simultaneous measurements of the Left Atrium pressure with a catheter and trans-esophageal Doppler echocardiography published in the article "Noninvasive assessment of left atrial maximum dP/dt by a combination of transmitral and pulmonary venous flow", see the Journal of the American College of Cardiology, V. 34, Issue 3, September 1999, P. 795-801, by Satoshi Nakatani, Mario J Garcia, Michael S Firstenberg, Leonardo Rodriguez, Richard A Grimm, Neil L Greenberg, Patrick M McCarthy. However, in this article it had not been reflected that not only Doppler echocardiography but a regular ultrasound or other imaging methods can be used to assess the atrial and more important ventricular (both left and right maximal dP/dt values called Left/Right Ventricular Pressure Rise) blood pressure and not only pressure changes, but absolute pressure values as well. This principle is realized in the present invention.

This present disclosure contains amongst others a novel method to calculate and determine the intracardiac pressure and the proposed method is independent of the frequencies of both the direct and reflected signals. Thus, prior technical solutions, such as disclosed in U.S. Pat. Nos. 5,619,997 A, 5,989,190 A, 6,083,165 A, or US 20030176789 are not analogues both in the methods of data collection and the methods of data processing of the current disclosure.

The approach in the present disclosure is based on the estimation of the pressure as a function of volumes of oscillating traceable regions (e.g. heart chambers) conducted via image processing of ultrasound (or other imaging device with similar functionality) recording.

Additionally, the present disclosure contains a provision for utilizing real-world data for increasing performance and accuracy obtained by calibration procedure, which contains synchronized simultaneous measurement recordings of the intra-cardiac blood pressure, such as with a micro-manometer catheter, and imaging device recordings, performed in case a user undergoes a routine or diagnostic cardiac catheterization for any medical reason.

SUMMARY OF THE INVENTION

The essence of the current disclosure lies in the description of a direct non-invasive method of measurement of the intracardiac blood pressures and an apparatus for its practical implementation.

The apparatus contains a medical imaging device capable of highlighting inner physiological features and streaming image data in real time and is configured to produce an image stream $\{J_i\}_{i=1, \ldots N}$ (where i is the index of the image and N is the number of images in the stream) of cardiovascular movement, and a processor unit (a computer or mobile device) which is configured to receive the image stream through a communication protocol and index the images by corresponding time-stamps. The processor unit records, processes the image stream and calculates the blood pressure in the given volume of the cardiovascular structure.

The method provided in the present disclosure is intended for calibration, measurement and calculation of intracardiac blood pressure based on the volumes of cardiovascular structures including but not limited to the Left Atrial Pressure (LAP), Right Atrial Pressure (RAP), Left Ventricular Pressure Rise $dP/dt_{max,L}$ (LVPR), Right Ventricular Pressure Rise $dP/dt_{max,R}$ (RVPR), Pulmonary Artery Pressure (PAP), Left Ventricular Systolic Pressure (LVSP), and Right Ventricular Systolic Pressure (RVSP), Left Ventricular End-Diastolic Pressure (LVEDP) and Right Ventricular End-Diastolic Pressure (RVEDP).

The pressure values within the above positions may provide valuable diagnostic information for potential therapeutical treatment of a user, for example, markers of the right heart failure, cardiomyopathy, right ventricular ischemia and infarction, left heart failure (CHF), myocardial infarction, tamponade, aortic regurgitation and others.

While the change in shape and size of the heart as seen on ultrasound, MRI or CT does reflect the changes in intracardiac pressure and the markers for changing of the heart condition can be obtained by the currently proposed system completely non-invasively, the exact value of the pressure is still unknown as it differs from person to person and depends on a variety of physiological factors.

To solve this, we introduce the calibration procedure, which takes advantage of the fact that catheterizations for pressure measurement or other diagnostic or treatment purposes are routinely performed on patients with conditions that make them the primary potential users of the current invention, and subsequently requires only to add a parallel ultrasound recording to any other performed actions in order to obtain two parallel streams of data: ultrasound and pressure. The system compares them and produces a personal formula—a calibration model, which would be valid for the user henceforth. Following the calibration procedure, this model can help the user to measure and detect any changes in the intracardiac pressure in non-invasive way at any place and time of choice and alert the user and connected medical service provider if the changes signal worsening of the health condition.

The present invention relies on a usage of medical imaging devices, such as ultrasound, MRI or CT devices, which are capable to produce a time series of images highlighting the boundaries, shape, size and position of inner physiological features such as heart chambers while being positioned fully outside of the body and communicating this series of images in real time to a processor for subsequent analysis.

The series of images (frames) obtained from the imaging device image stream $\{J_i\}_{i=1, \ldots N}$ which hereafter is referred as the T-image, is a 3-dimensional cube of imaging data consisting of individual pixels, where the axes are longitudinal and lateral coordinates of the pixel within the image, the time of frame recording, and the values are brightness and/or color values of the pixel.

The processing software determines the boundaries, shape, size and position of the heart chambers on each of the frames and traces the movement of pixels from image to image to determine their change over time. As the heart beats, the coordinates of the visible boundaries will change to reflect the contraction and expansion, and from the change of those boundaries a change in blood pressure will be derived.

In order to simplify the processing and to enable user-friendly visualization of the T-image, the so-called Characteristic image can be used, which is a form of height-by-time projection where each frame is compressed to a single column. The Characteristic image presents the vertical movement of the heart boundaries. Assuming the imaging device is correctly positioned, the vertical movement will roughly correspond to pressure changes, and its accuracy can be further expanded by more detailed analysis of each of the images.

The present invention is defined by the enclosed patent claims. The advantages of the disclosed method over the prior art presented by this disclosure include:

Estimation of intracardiac pressure changes as function of the observed changes in the size and position of oscillating traceable regions within the vicinity of the heart during non-invasive measurements;

Calibration procedure, which is performed during routine diagnostic catheterization procedure one time per user, and is a synchronized, simultaneous measurement of intra-cardiac blood pressure with a micro-manometer catheter attached to clinical catheterization pressure measurement monitor and a medical imaging device with subsequent image processing analysis and model fit for subsequent pressure calculation;

Usage of the imaging device in combination with the processor in order to calculate the intracardiac pressure by obtaining imaging data of the same region in the heart vicinity of the user and using the unique fitted functional parameters of the calibration model from the calibration procedure to evaluate the imaging data anytime, anywhere, not only for an individual user, but for a class of users with the similar physiological profile.

Process for the analysis of a series of images based on the new notions of:

- T-image $\{T_i\}_{i=1,\ldots N}$, (where i is the index of the image and N is the number of images in the stream) which is defined as a chronological union of image stream $\{J_i\}_{i=1,\ldots N}$ with corresponding time stamps.
- Characteristic (or Eigen-) Image $\{I_i\}_{i=1,\ldots N}$ of the T-image $\{T_i\}_{i=1,\ldots N}$, which is as a chronological union of the averages of the rows or other invariants of the image series $\{T_i\}_{i=1,\ldots N}$ across each given depth, in the way that the first pixel-column $I_1$ (i=1) of the Characteristic image contains the averages over the rows or other invariants of the first image in time, the second pixel-column $I_2$ (i=2) of the Characteristic image contains the averages over the rows or other invariants of the second image in time, and finally the last pixel-column $I_N$ (i=N) of the Characteristic image contains the averages over the rows or other invariants of the last image in time in the series. Characteristic image method reduces the problem dimensionality while still permits to identify the pressure curve, provides a considerable boost in performance and lowers calculation power requirements which is useful for small or embedded devices.
  The invariants in the Characteristic images can be
    averages of the columns
    vertical or horizontal average gradients
      singular values or eigenvalues of each image packed into the Characteristic image as one matrix
      Fourier, Wavelet or other generalized decomposition images of the Characteristic images defined above.

Additionally, the Characteristic image shows the dynamics of movement of the oscillating traceable regions.

The above Process for the analysis of a series of images includes two major procedures:
  Calibration procedure, where the pressure in the target region, acquired from catheterization pressure measurement monitor and corresponding imaging data are both known and the goal is to build a calibration model of the pressure as a function of imaging data and including the following method steps:
    aligning the directly measured intra-cardiac chamber pressures during catheterization with synchronized imaging data
    processing the image stream $\{J_i\}_{i=1,\ldots N}$ and generate corresponding T-image $\{T_i\}_{i=1,\ldots N}$
    processing the T-Image $\{T_i\}_{i=1,\ldots N}$ to determine oscillating traceable regions corresponding to cardiovascular structures in heart vicinity and record their shape changes over time,
    creating a set of coordinate parameters $\{x_j\}_{j=1,\ldots M}$ (where j is an index of the coordinate and M is the total number of the coordinate parameters) representing the oscillating traceable region size, shape and position at each time corresponding to each frame $T_i$ of the T-image $\{T_i\}_{i=1,\ldots N}$, and
    fitting the functional parameters of the calibration model capable to further calculate the pressure function P inside an oscillating traceable region according to the measured, intra-cardiac chamber pressures during catheterization. The functional parameters of the pressure function P are chosen to perform the best fit between the measured $\hat{P}_i$ and estimated pressure values $P_i = P(t_i, \{x_j\}_{j=1,\ldots M}^i \subset T_i)$ of a shape and position of the oscillating traceable region.
    In case of using T-Image $\{T_i\}_{i=1,\ldots N}$ itself, the function is $P(t_i) = P(t_i, \{x_j\}_{i=1,\ldots M}^i \subset T_i)$, where $x_j$ are a set of coordinate parameters representing the oscillating traceable region boundaries and position at each time corresponding to each frame $T_i$ of the T-image $\{T_i\}_{i=1,\ldots N}$.
    In case of using Characteristic image $\{I_i\}_{i=1,\ldots N}$ of the T-image $\{T_i\}_{i=1,\ldots N}$, being a process which simplifies the model reducing its dimension and significantly improves calculation times without significant precision loss, $P_i = P(t_i, \{x_k\}_{j=1,\ldots K}^i \subset I_i)$, where $\{x_j\}_{j=1,\ldots K}$ are a set of coordinate parameters representing the oscillating traceable region size and position at each time corresponding to each column $I_i$ of the Characteristic Image $\{I_i\}_{i=1,\ldots N}$.

Usage procedure, where the imaging data and the previously acquired calibration model for calculation of the pressure as a function of imaging data are known, and the goal is to estimate the pressure values using the previously acquired model from the imaging data and including the following method steps:
    processing the image stream $\{J_i\}_{i=1,\ldots N}$ and generate corresponding T-image $\{T_i\}_{i=1,\ldots N}$
    processing the T-Image $\{T_i\}_{i=1,\ldots N}$ to determine oscillating traceable regions corresponding to cardiovascular structures in heart vicinity and record their shape changes over time,
    creating a set of coordinate parameters $\{x_j\}_{j=1,\ldots M}$ representing the oscillating traceable region size, shape and position at each time corresponding to each frame $T_i$ of the T-image $\{T_i\}_{i=1,\ldots N}$, and
    applying the function $P_i = P(t_i, \{x_j\}_{j=1,\ldots M}^i \subset T_i)$ produced during the calibration procedure to the above set of coordinate parameters to estimate the pressure values at each time corresponding to each frame $T_i$ of the T-image $\{T_i\}_{i=1,\ldots N}$ and pressure changes between the frames. In the absence of calibration procedure for a particular user machine-learning tools permit to estimate the pressure basing on calibration data from other users with similar physiological parameters.

Accordingly, utilizing the data obtained during calibration procedure, the intracardiac pressure and its dynamic changes within the cardiovascular system can be calculated with high accuracy and stability any time after the calibration procedure when a recording of the calibrated region is provided with the medical imaging device coupled with the processor unit in the framework of the current apparatus.

A collection of fitted calibration models produced by the calibration procedure on various users enables to produce generalized calibration models that may be applied to additional users which have not undergone the calibration procedure during clinical catheterization, but have similar physiological characteristics to those that were calibrated.

BRIEF DESCRIPTION OF THE DRAWINGS

The below described embodiments with the references to the accompanying drawings present the features and advantages of the current invention. It has to be noted that being an example of a functional system the following implementation is not limited to mentioned devices/technologies that may be replaced by their similar modalities as long as those modalities can produce the imaging data and maintain data connections to processor units which, in turn, may be any computing devices restricted only by ability to run processing software and provide necessary data connections and user interfaces.

DESCRIPTION OF EMBODIMENTS

Specific embodiments or examples of the invention will now be described with reference to the accompanying drawings. This invention may, however, can be embodied in many different forms and should not be construed as limited to the embodiments demonstrated herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention.

The present description of the current invention is given with reference to heart chambers and major blood vessels in heart vicinity. It should be born in mind however that the present invention is not limited strictly to heart chambers and major blood vessels, but can be easily adapted to any medium transparent for ultrasound or other waves with the need to measure pressure changes of a liquid flow within a flexible environment.

Alternatively or in addition to ultrasound in order to generate series of images to be analyzed for the intracardiac pressure determination, other systems capable of highlighting inner physiological features and streaming image data in real time, for instance Magnetic Resonance Imaging (MRI), or ionizing radiation based imaging systems like Roentgen (X-Ray, Computer tomographic Imaging [CT]) can be provided as medical imaging modalities for generating the input for the pressure determination.

Additionally, while the present description refers to the usage of 2-dimensional cross-section ultrasound imaging of the investigated chamber as is produced by contemporary sensors, it is not limited to it and can utilize different modalities that produce several 2-dimensional cross-sections or a full 3-dimensional representation of the investigated chamber.

Figure 1:
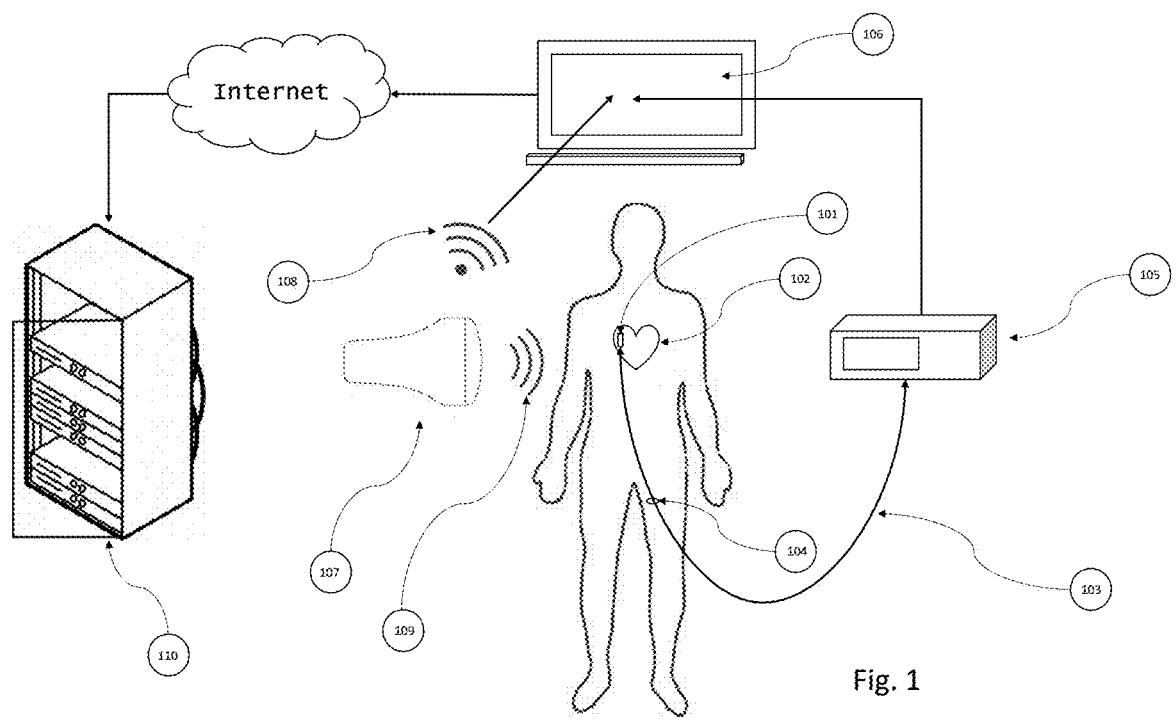
FIG. 1 depicts a schematic illustration of a blood pressure calibration procedure performed during clinical catheterization. The pressure sensor (101) is located inside the user's heart or major blood vessel in the heart vicinity (102) introduced by catheter (103) through a subclavian jugular or cephalic vein (104). The sensor is connected to pressure monitor (105), which is, in turn, connected to a computer, serving as the processor unit (106). The medical imaging device (107), connected to the processor unit (106) by wired or wireless connection (108), is performing a recording (109) of the user's heart (102) where the sensor (101) is located. The processor unit (106) creates a simultaneous recording from both imaging device (107) and pressure monitor (105), synchronizes the data, performs the calculations and stores them or sends them to remote cloud or other specialized server (110) for storage or performing calculations.

In accordance with preferred embodiments a system comprises for example of:
1) For the calibration procedure (FIG. 1)
a) At least one catheter based intracardiac blood pressure sensor (101) with analogue or digital data output connected to a standard clinical catheterization pressure measurement monitor (105). The intracardiac blood pressure sensor is located inside one of the user's heart chambers or surrounding blood vessels, such as pulmonary artery, (102) introduced, for example, by catheter (103) through a subclavian, jugular or cephalic vein (104). It is assumed, however, that since the calibration procedure is performed during routine scheduled clinical catheterization for the user, the sensor may be already introduced into the problematic region as a part of a medical procedure, then only its connection to the processor unit as described in items b) and d) below is actually required.

b) Medical pressure measurement monitor with digital data output permitting to receive the pressure data from the pressure sensors (101) and stream the output data into the processor unit, which can be a computer or mobile device (106). This functionality can be encapsulated inside either pressure monitor or processor unit in alternative embodiments.

c) At least one medical imaging device, for example an ultrasound probe (107) with wired or wireless digital output permitting to stream the output data into the processor unit (106). The ultrasound probe is pointed to the same cardiac region where the sensor (101) is located.

d) Processor unit, preferably a computer or a mobile device equipped with hardware and software permitting synchronization, recording, storage and processing of input data from medical imaging device and medical pressure monitor. The processor unit performs a simultaneous recording 30-60 seconds from both medical imaging device and pressure measurement monitor.

Figure 2:
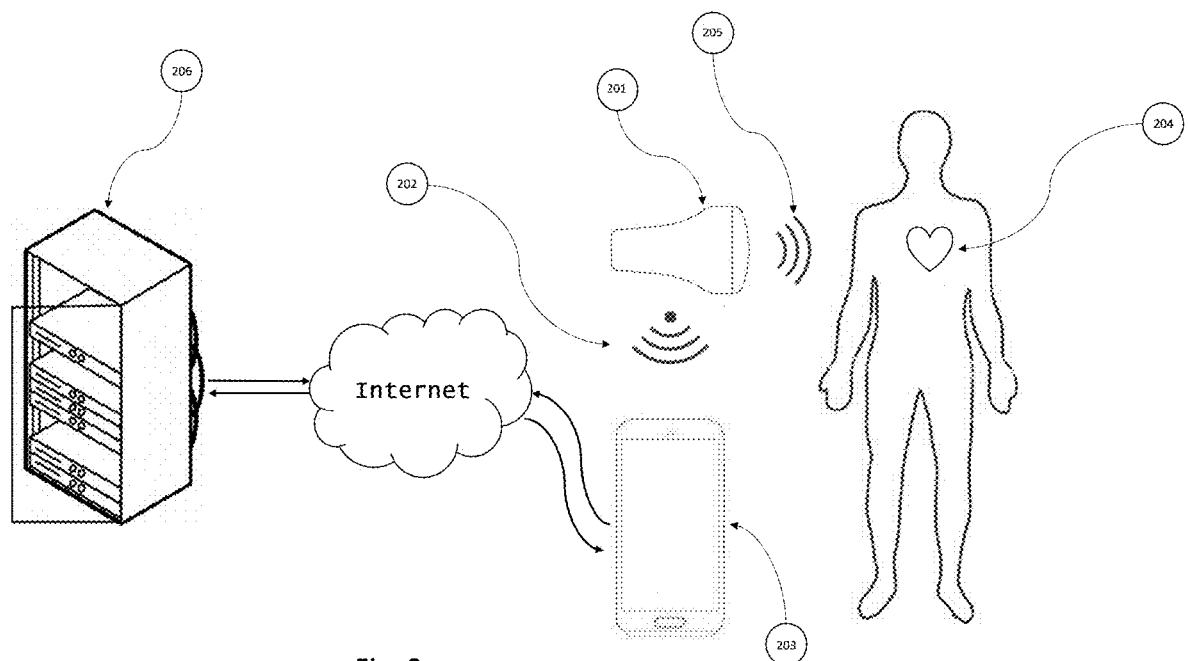
FIG. 2 depicts the typical usage procedure of the pressure measurement method. The imaging device (201), connected by wired or wireless connection (202) to processor unit (203), is pointed towards the user's heart (204), for which the calibration procedure was previously performed and performs a recording (205), sending it to the processor unit. The processor unit either performs the calculations locally or sends the data to remote cloud server or other specialized server (206). The calculations are performed based on previously recorded model and their results are displayed to the user through the UI on the processor unit.

2) For the General (or post-calibration) Usage Process (FIG. 2)

a) At least one medical imaging device, for example an ultrasound probe (201) with wired or wireless digital output permitting to stream the output data into the processor unit (203). Processor unit (203), which can be a computer or a mobile device equipped with hardware and software permitting recording, storage and processing of input data from medical imaging device.

3) Optionally the system may include a remote cloud or other specialized server (110, 206, 302, and 402), operation of which permits both processor units (106, 203) to store, retrieve and exchange data if internet connection is available, but it is generally possible to transfer the data by other means, directly between the devices or by physical medium.

4) During the calibration procedure, the software, positioned either on the processor unit (106) or on remote cloud or other specialized server (110) processes the recorded data by using the algorithm described in items 7)-9), creates and stores a calibration model (303) for calculation of subsequent pressure results from medical imaging device unit recordings of the previously calibrated user. This model is transferred directly or via the server to the processor unit.

Figure 3:
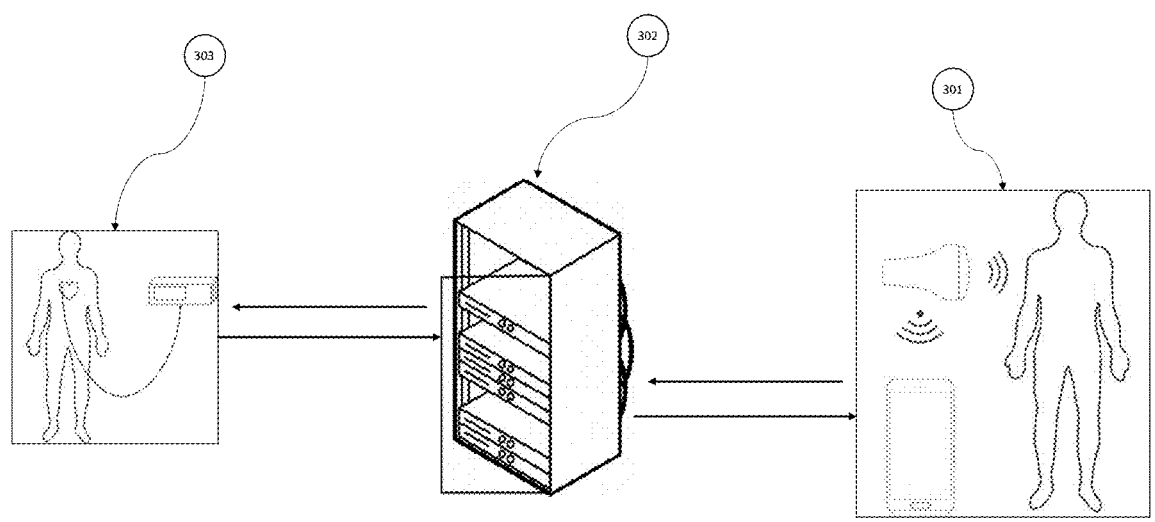
FIG. 3 depicts the typical case of usage procedure in presence of previously recorded calibration model for the user, who performs the measurement procedure (301), sending the data to remote cloud or other specialized server (302), which retrieves the stored calibration model (303) and calculates the result according to the calibration model.

5) During the General Usage Process (FIG. 3, 4) the calibration model (303) is accessed either locally or on server (302) by processor unit to calculate the user's intracardiac pressure according to the data recorded by the imaging device (202).

Figure 4:
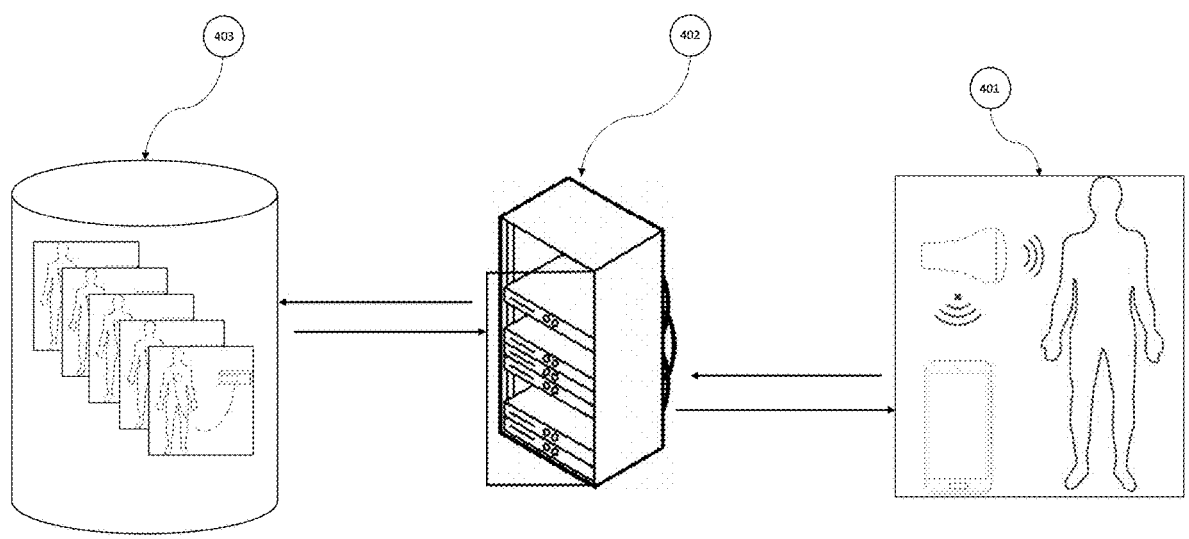
FIG. 4 depicts the typical case of usage procedure without previous calibration model for the user. The user performs the recording procedure (401), sending the data to remote cloud or other specialized server (402), which retrieves the stored calibration models (403) of other users with similar physiological data (age, weight, height, diagnoses, etc.) and uses machine learning to calculate the result according to calibration models.

6) In absence of previous calibration model for the specific user (FIG. 4) the user performs the recording procedure (401), sending the data to remote cloud or other specialized server (402), which retrieves the stored calibration models (403) of other users with similar physiological profile (age, weight, height, diagnoses, etc.) and uses machine learning to calculate the result according to calibration models. In this case use of a server is required.

Figure 5:
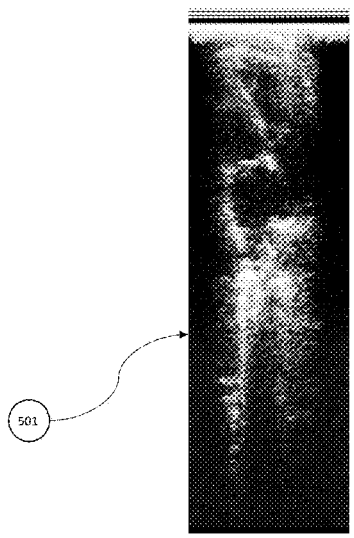
FIG. 5 depicts a single frame of imaging data of the user's heart (501) as it is received from imaging device.
Figure 6:
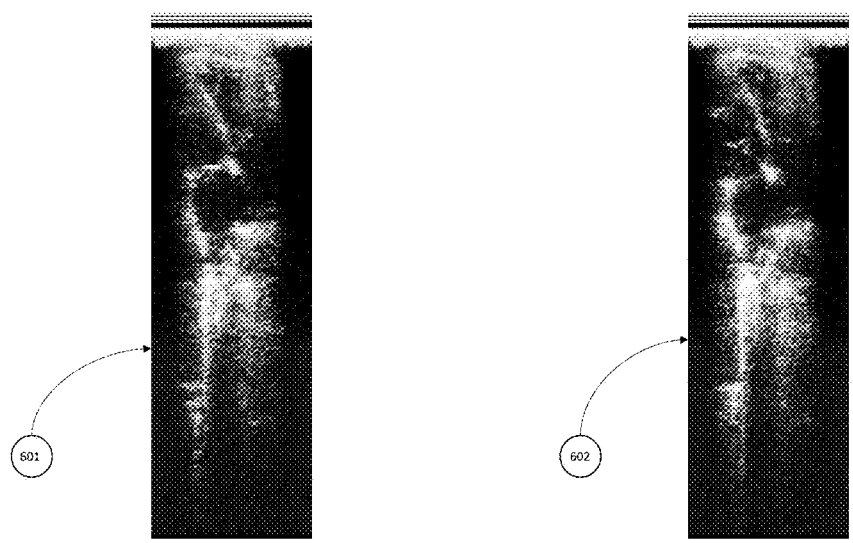
FIG. 6 depicts two frames of imaging data of the user's heart showing the difference between imaging data at different time moments (601, 602).
Figure 7:
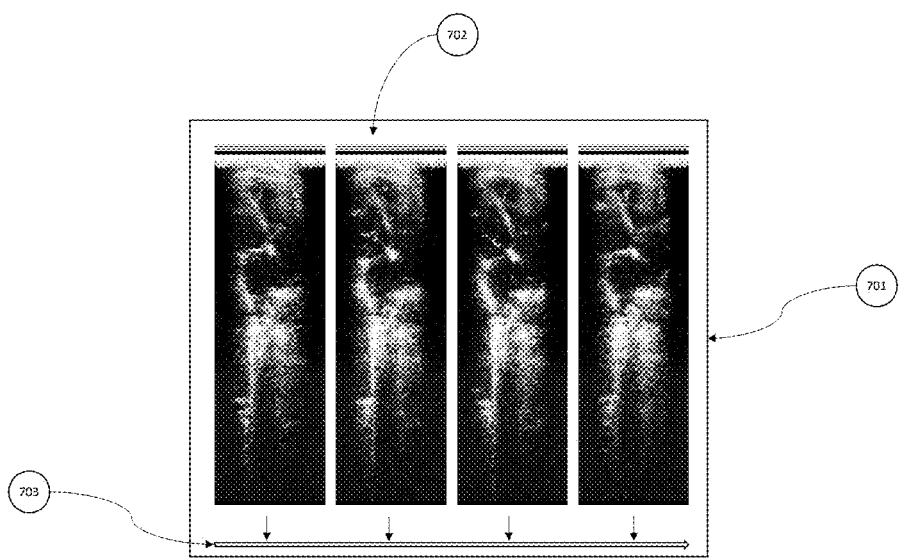
FIG. 7 depicts the assembled T-Image (701) compiled from imaging data (702) with an appropriate time axis (703).
Figure 8:
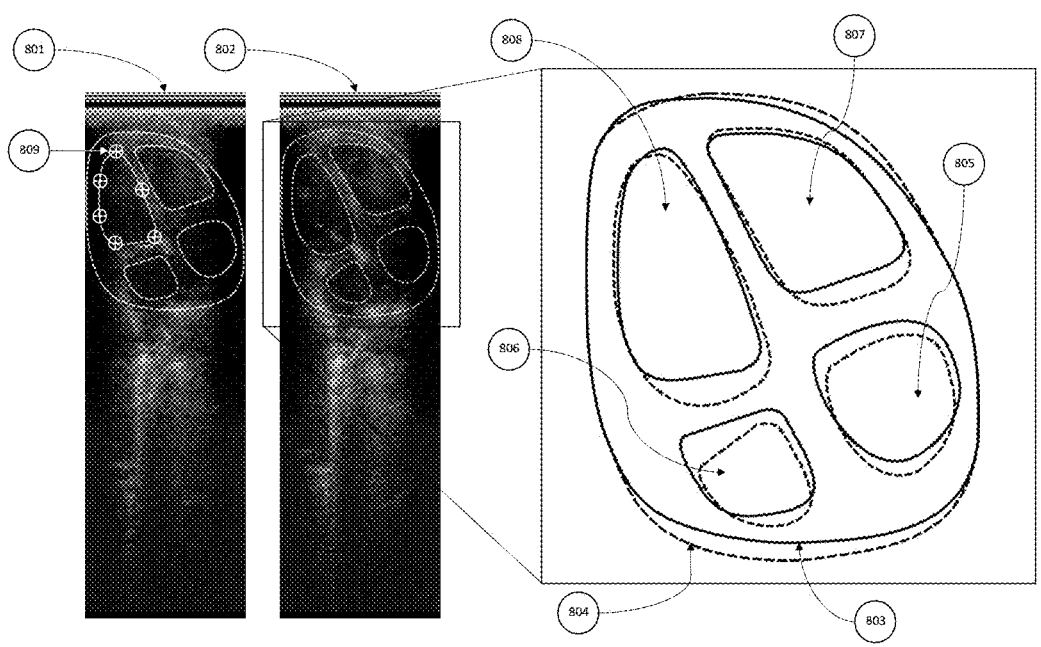
FIG. 8 depicts two frames of imaging data (801, 802) in different states of the heart movement with detected heart chamber contours (803, 804), and the positions and contours of Right Atrium (805), Left Atrium (806), Right Ventricle (807) and Left Ventricle (808). In the first frame the contour (803) is depicted as formed from a sample set of coordinate parameters $\{x_1\}$ (809) that are used during calculation.
Figure 9:
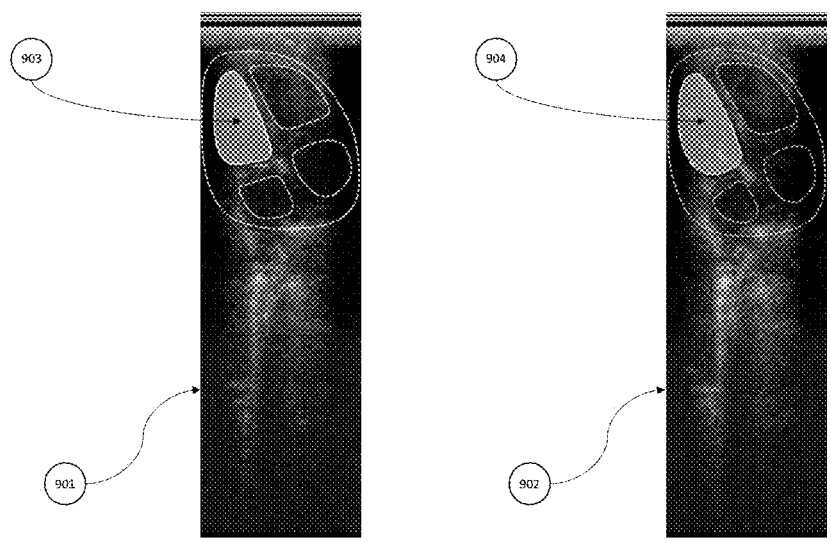
FIG. 9 depicts two frames of imaging data (901, 902) with separated contours of Left Ventricle (903, 904) at subsequent time stamps.
Figure 10:
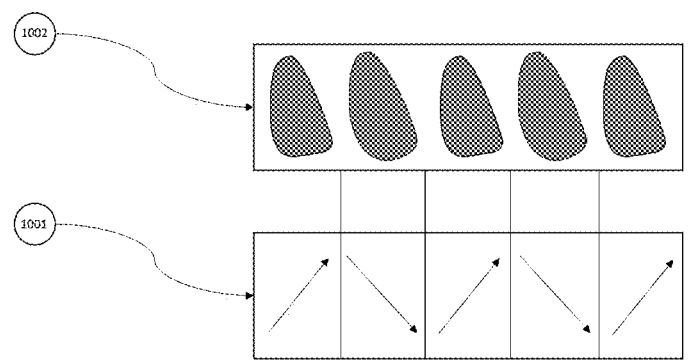
FIG. 10 depicts the connection between pressure (1001) and state of heart chamber, in case of the Left Ventricle (1002).

7) The data recorded during the calibration procedure is processed as follows:

a) The data received from the imaging device decoded into image frames (FIG. 5).

b) Each frame (FIG. 6) is marked with a time stamp at which it was recorded. In this example the difference between frames (601) and (602) is about 0.5 second.

c) T-Image $\{T_i\}_{i=1,\ldots N}$ (FIG. 7) (701) is formed from the data. It comprises an array of imaging data (702) linked to an appropriate time axis (703) and the simultaneously measured intracardiac pressure values $\{\hat{P}_i\}_{i=1,\ldots N}$ obtained by the intracardiac pressure measurement monitor in the target oscillating traceable region(s) which can be for example the Right/Left Atrium, Right/Left Ventricle, or other major blood vessels in heart vicinity.

d) The software determines the physiological features that can be detected in the imaging data (FIG. 8). On the two frames (801, 802) separated in FIG. 8 by 0.5 second, the software locates the heart (803, 804), and the positions and contours of oscillating traceable region(s) as the Right Atrium (805), Left Atrium (806), Right Ventricle (807) and Left Ventricle (808). The physiological features are determined through the set of coordinate parameters $\{x_1\}$(809), representing the form of the target region. This coordinate set may contain any number of point coordinates, depending on the processing power available to the software and image resolution of the imaging device, with at least two point coordinates (the depths where the target region begins and where it ends) required to make a pressure assessment.

e) If, for example, the sensor during the calibration procedure was located in the Left Ventricle (FIG. 9) of the user's heart, the software separates the Left Ventricle (903, 904) on each frame (901, 902) according to the detected contour (903, 904) represented by a set of coordinates $\{x_j\}$.

f) The software then compares (FIG. 10) the changes in coordinate sets in each frame (1002) to the changes in pressure (1001) measured at the same time, and builds a calibration model by fitting the measured pressure to a calibration model $P(t_i)=P(t_i, \{X_j\}_{j=1,\ldots M}^i \subset T_i)$, where $P(t_i)$ is the calculated pressure at time $t_i$ of each imaging frame and where for each input set of coordinate parameters $\{x_j\}_{j=1,\ldots M}^i$ the result would be as close as possible to the corresponding intracardiac pressure values $\{\hat{P}_i\}_{i=1,\ldots N}$.

g) The calibration model, is stored in the processor unit and later transferred to the user's processor unit using a cloud or other specialized server or directly or by any other means.

Figure 11:
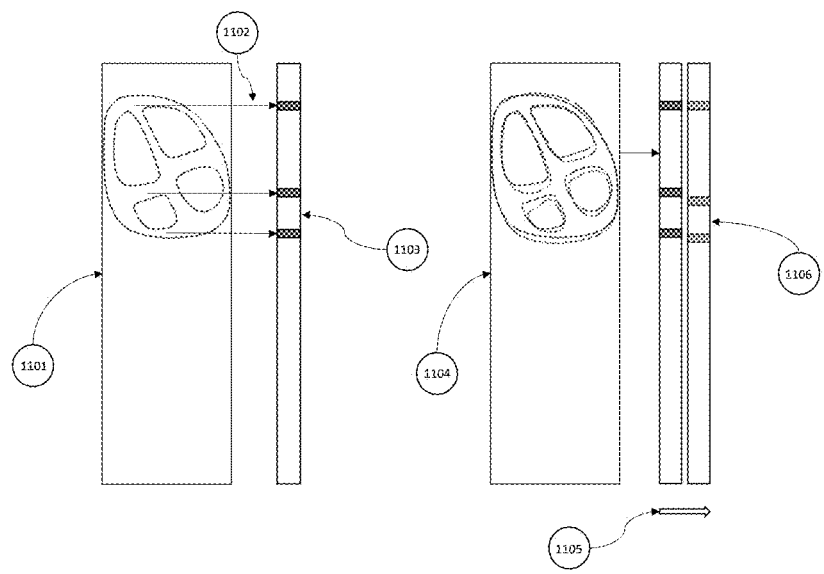
FIG. 11 depicts the process of creation of a Characteristic Image. A frame of imaging data (1101) is compressed (1102) to a single column (1103) using averaging or other invariant method to mark the vertical positions of heart tissue. In the same manner, the T-Image (1104) containing series of frames and a time axis (1105) is compressed to a Characteristic Image (1106) with number of columns identical to number of frames, illustrating the tissue movement over time.
Figure 12:
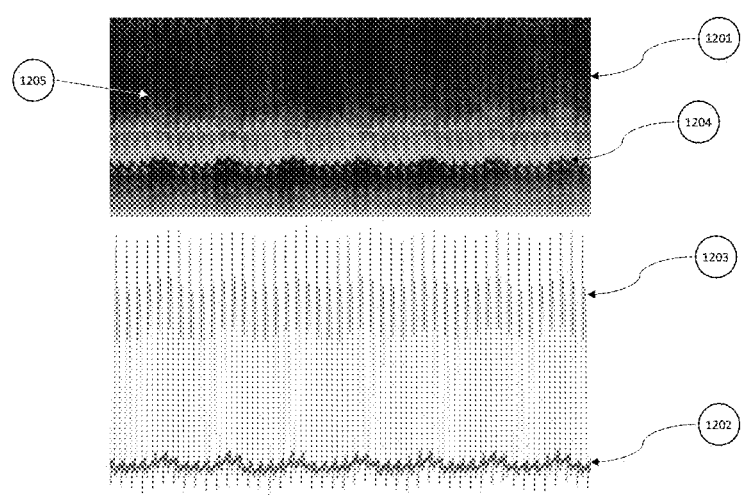
FIG. 12 illustrates the similarity between Characteristic Image (1201) and pressure measurements of LA (1202) and LV (1203) as received from the pressure monitor (105). The LA (1204) and LV (1205) pressure curves are clearly identifiable on the Characteristic Image (1201).

8) Additionally to the method described above in item 7) a method of processing for simplified detection of regions of interest may be used:

a) Conversion of T-Image into a Characteristic Image (FIG. 11). Each frame $\{T_i\}_{i=1,\ldots N}$ of imaging data (1101) is compressed (1102) using averaging or other invariant method to a single column (1103). In the same manner, the T-Image (1104) containing series of frames and a time axis (1105) is compressed to a Characteristic Image (1106) with number of columns identical to number of frames and the same time axis.

b) The software determines the positions of the target oscillating traceable regions by tracing their movement over time (1204, 1205) on the compressed columns. The similarity (FIG. 12) between the synchronized pressure measurements of LA (1202) and LV (1203) as received from the pressure monitor (105) and the respective calculated pressure curves LA (1204) and LV (1205) in the Characteristic Image (1201) is clearly identifiable. The identified positions are passed to more detailed analysis as described in 7).

9) During General Usage, the user
a) Uses the imaging device in the same manner as during the calibration procedure to make a recording for a of a preset time period while pointing at the same region that was recorded during the calibration procedure. The region and angle to which the imaging device is directed are marked during the calibration procedure and made available to the user via graphical user interface (GUI).
b) The imaging device transmits by wired or wireless connection the image sequence to the processor unit.
c) The processor unit retrieves the user's model (if the user had undergone personal calibration procedure) from internal memory/cloud service/storage medium.
d) If the user did not undergo the personal calibration procedure, the processor unit transmits the user's data such as height, weight, diagnosis, stored in similar way to the cloud service or specialized server. The cloud service or specialized server returns a model created using machine learning based on the database of calibrated models for users with similar characteristics.
e) The software on the processor unit then processes the images obtained from the imaging device during the recording in a manner similar to items 7(d)-7(f) or 9), obtaining the coordinate set $\{x_j\}$.
f) Using the coordinate set $\{x_j\}$ and the model $P(t_i)=P(t_j, \{x_j\}_{j=1,\ldots M}^i \subset T_i)$, the software calculates its assessment of pressure and displays it to the user.
g) The software may optionally transmit this assessment to the server, display it to the doctor using doctor's dedicated system and/or show system alerts if it detects abnormal values or patterns.

10) The other real time characteristics which can be measured or estimated using the described system include but not limited to: Left Atrial Pressure (LAP), Right Atrial Pressure (RAP), Left Ventricular Pressure Rise $dP/dt_{max,L}$ (LVPR), Right Ventricular Pressure Rise $dP/dt_{max,R}$ (RVPR), Pulmonary Artery Pressure (PAP), Pulmonary Capillary Wedge Pressure (PCWP), Left Ventricular Systolic Pressure (LVSP), and Right Ventricular Systolic Pressure (RVSP), LVEDP (Left Ventricular End-Diastolic Pressure) and RVEDP (Right Ventricular End-Diastolic Pressure).

11) The system includes software with at least the following capabilities:
a) Both processor units used during the calibration procedure and for general usage may be any computing devices restricted only by ability to run processing software and provide necessary data connections and user interfaces.
b) For the processor unit during calibration procedure the software will:
  i) Provide a real-time connection for data retrieval from
    (1) Medical imaging device
    (2) Pressure sensor(s) and/or a Pressure Monitor
  ii) Display the images and pressure data acquired from above devices, including image stream for targeting the region of interest.
  iii) Provide assistance in targeting for the user on GUI.
  iv) Perform a synchronized data recording from medical imaging device and pressure monitor.
  v) Store and transmit the acquired data to readable medium, other devices or cloud server.
  vi) Perform analysis and fitting of pressure calibration model based on acquired data.
c) For Processor unit during general usage the software will:
  i) Provide a real-time connection for data retrieval from medical imaging device.
  ii) Display the images and pressure data acquired from the imaging device, including image stream for targeting the region of interest.
  iii) Provide assistance in targeting for the user on GUI.
  iv) Perform a recording of a preset length from medical imaging device.
  v) Store and transmit the acquired data to readable medium, other devices or cloud server.
  vi) Store and retrieve the calculation mode from internal memory, readable medium or the cloud server.
  vii) Perform a calculation of pressure based on calibration model and acquired data.
  viii) Detect anomalies and display alerts on user interface.
d) For cloud or dedicated server system:
  i) Store and retrieve user data, recordings and calibration models.
  ii) Provide user data to respective medical service providers including recording results, pressure trends, etc.
  iii) Collect and provide cumulative models from users with similar characteristics for users without personal calibration procedure.
  iv) Perform all analysis and calculations similar to processor units (12(b), 12(c)).
  v) Provide user interfaces for medical service providers and users.
  vi) Provide connection interfaces for processor units.

The present invention has been described using a non-limiting detailed description of various embodiments and examples thereof. It should be appreciated that the present invention is not limited by the above-described examples and that one ordinarily skilled in the art can make changes and modifications without deviation from the scope of the invention as will be defined below in the appended claims.

Within the scope of invention as defined by the appended claims the medical imaging device can be combined with the processor unit into a single device.

It should also be appreciated that features disclosed in the foregoing description, and/or in the foregoing drawings and/or following claims both separately and in any combination thereof, be material for realizing the present invention in diverse forms thereof. When used in the following claims, the terms "comprise", "include", "have" and their conjugates mean, "including but not limited to".

The present invention has been described above with reference to specific examples. However, other embodiments than the above described are equally possible within the scope of the invention. Different method steps than those described above, performing the method by hardware or software, may be provided within the scope of the invention. The different features and steps of the invention may be combined in other combinations than those described. The scope of the invention is only limited by the appended patent claims.

We claim:
1. A system for non-invasive measurement of intracardiac pressure comprising:
a medical imaging device capable of highlighting cardiovascular structures, including heart chambers and blood vessels connected to the heart of a user, and a processor unit equipped with software configured to calculate dynamically changing intracardiac pressures of the user;

wherein the system is assembled and prepared by the user or an external operator, which:

connects the medical imaging device to the processor unit, activates and points the medical imaging device towards the user's cardiac region;

wherein the assembled system is further controlled by the user or the external operator by activating the processor unit, which:

synchronizes the medical imaging device with the processor unit, receives an image stream $\{J_i\}_{i=1,\ldots N}$ from the medical imaging device, stores the image stream and generates a corresponding T-image $\{T_i\}_{i=1,\ldots N}$, which is defined as chronological union of the image stream $\{J_i\}_{i=1,\ldots N}$ with corresponding timestamps, following the creation of the T-image $\{T_i\}_{i=1,\ldots N}$ from the imaging data obtained from the medical imaging device, the processor unit further identifies a set of coordinate parameters $\{x_j\}_{j=1,\ldots M}^i$ (where i is an index of the image, j is an index of the coordinate parameter and M is the total number of the coordinate parameters) representing an oscillating traceable region size and position on each frame $T_i$ of the T-image $\{T_i\}_{i=1,\ldots N}$, by means of image processing, estimates the size, shape and positions of the target oscillating traceable region(s) from each frame of the T-image $\{T_i\}_{i=1,\ldots N}$, based on the obtained set of coordinate parameters $\{x_j\}_{j=1,\ldots M}^i$, estimates pressure values $P_i$ iterating from frame to frame of T-image $\{T_i\}_{i=1,\ldots N}$, based on the change in the size and position of the oscillating traceable region(s), stores on local computer medium or transmits via connection to a server, the T-Image, the set of coordinate parameters of the oscillating traceable region(s) and the estimated pressure values $P_i$, displays the series of pressure values $P_i$ on a graphical user interface (GUI).

2. The system of claim 1, wherein the processor unit is further configured to perform the following procedures:

creation of a calibration model for precise measurement of intracardiac pressure from the image stream obtained from the medical imaging device during a calibration procedure, which is performed during a clinical catheterization of the user, wherein the calibration procedure utilizes the system from claim 1 with an addition of an intracardiac pressure measurement monitor, and wherein the system is assembled and prepared by the external operator which:

connects the medical imaging device to the processor unit using wired or wireless connection, connects the intracardiac pressure measurement monitor to the processor unit configures the intracardiac pressure measurement monitor to receive intracardiac pressure values $\{\hat{P}_i\}_{i=1,\ldots N}$ from pressure sensors located inside user's cardiovascular structures such as heart chambers and major blood vessels connected to the heart and to transmit the intracardiac pressure values to the processor unit, activates and points the medical imaging device towards user's cardiac region;

wherein the assembled system is further controlled by the external operator by activating the processor unit, which:

synchronizes the medical imaging device and the intracardiac pressure measurement monitor with the processor unit, receives the image stream $\{J_i\}_{i=1,\ldots N}$ from the medical imaging device, stores the image stream and generates the corresponding T-image $\{T_i\}_{i=1,\ldots N}$, receives the measured intracardiac pressure values $\hat{P}_i$ from the intracardiac pressure measurement monitor simultaneously with the receiving of the image stream $\{J_i\}_{i=1,\ldots N}$ from the medical imaging device, the processor unit further:

performs the steps from claim 1 to determine the size, shape and positions of the oscillating traceable region(s) and creates a set of coordinate parameters $\{x_j\}_{j=1,\ldots M}^i$;

assigns to each frame $T_i$ the set of coordinate parameters $\{x_j\}_{j=1,\ldots M}^i$ and the measured intracardiac pressure value $\hat{P}_i$, for all the frames $T_i$, using a functional fit, creates the calibration model $P_i = P(t_i, \{x_j\}_{j=1,\ldots M}^i \subset T_i)$ as a function, where for each input set of coordinate parameters $\{x_j\}_{j=1,\ldots M}^i$ the result would be as close as possible to the measured intracardiac pressure values $\{\hat{P}_j\}_{i=1,\ldots N}$, stores on local computer medium or transmits via connection to the server the T-Images, the sets of the oscillating traceable region(s) and the calibration model; and usage of the calibration model for precise measurement of intracardiac pressure from the image stream obtained from the medical imaging device, wherein the processor unit:

retrieves from a local computer medium or via connection from the server the calibration model, applies the calibration model $P_i = P(t_i, \{x_j\}_{j=1,\ldots M}^i \subset T_i)$ to the set of coordinate parameters $\{x_j\}_{j=1,\ldots M}^i$, producing a series of calculated intracardiac pressures $P_i$, displays the series of calculated intracardiac pressures $P_i$ on graphical user interface (GUI).

* * * * *